(12) United States Patent
Zhou et al.

(10) Patent No.: US 11,938,041 B2
(45) Date of Patent: Mar. 26, 2024

(54) PASSAGE ESTABLISHMENT DEVICE FOR POSTERIOR SPINAL FUSION MINIMALLY INVASIVE SURGERY

(71) Applicant: SHANGHAI SANYOU MEDICAL CO., LTD., Shanghai (CN)

(72) Inventors: Yue Zhou, Shanghai (CN); Changqing Li, Shanghai (CN); Mingyan Michael Liu, Shanghai (CN); Xing Liu, Shanghai (CN)

(73) Assignee: SHANGHAI SANYOU MEDICAL CO., LTD., Shanghai (CN)

( * ) Notice: Subject to any disclaimer, the term of this patent is extended or adjusted under 35 U.S.C. 154(b) by 509 days.

(21) Appl. No.: 17/273,735

(22) PCT Filed: Jun. 26, 2019

(86) PCT No.: PCT/CN2019/093000
§ 371 (c)(1),
(2) Date: Apr. 12, 2021

(87) PCT Pub. No.: WO2020/048193
PCT Pub. Date: Mar. 12, 2020

(65) Prior Publication Data
US 2023/0285166 A1   Sep. 14, 2023

(30) Foreign Application Priority Data
Sep. 7, 2018 (CN) .......................... 201811044794.6

(51) Int. Cl.
*A61F 2/46* (2006.01)
*A61B 17/02* (2006.01)

(52) U.S. Cl.
CPC ........ *A61F 2/4611* (2013.01); *A61B 17/0218* (2013.01); *A61B 17/025* (2013.01);
(Continued)

(58) Field of Classification Search
CPC . A61F 2/4611; A61B 17/0218; A61B 17/025; A61B 17/3421; A61B 17/3423
See application file for complete search history.

(56) References Cited

U.S. PATENT DOCUMENTS 6,224,599 B1   5/2001   Baynham et al.
2016/0007983 A1   1/2016   Frey et al.
(Continued)

FOREIGN PATENT DOCUMENTS

CN   103405213 A   11/2013
CN   203280430 U   11/2013
(Continued)

*Primary Examiner* — Si Ming Ku
(74) *Attorney, Agent, or Firm* — IPRTOP LLC (57) ABSTRACT

The present disclosure relates to the technical field of medical instrument and provides a passage establishment device for posterior spinal fusion minimally invasive surgery. The device includes: a tube, an interior of the tube includes a through hole penetrating through both axial ends of the tube, and a wall of the tube includes an opening portion. The tube of the passage establishment device of the present disclosure can be inserted between the vertebral bodies and can also be removed from between the vertebral bodies. The through hole of the tube forms a surgical passage for the fusion device to penetrate, which can safely protect human tissues and is convenient for doctors to perform follow-up operations. The tube can be installed quickly, and thus the operation time is shortened. It is easy to disassemble, clean, and disinfect the tube.

7 Claims, 7 Drawing Sheets

(52) U.S. Cl.
CPC ............ *A61B 2017/0256* (2013.01); *A61F 2002/4635* (2013.01)

(56) References Cited

U.S. PATENT DOCUMENTS

| | | | |
|---|---|---|---|
| 2017/0333023 | A1 | 11/2017 | Adams |
| 2019/0008656 | A1* | 1/2019 | Salvermoser ......... A61F 2/4611 |

FOREIGN PATENT DOCUMENTS

| | | |
|---|---|---|
| CN | 204542245 U | 8/2015 |
| CN | 204600638 U | 9/2015 |
| CN | 206934128 U | 1/2018 |
| CN | 109480926 A | 3/2019 |
| IN | 207755309 U | 8/2018 |

\* cited by examiner

PASSAGE ESTABLISHMENT DEVICE FOR POSTERIOR SPINAL FUSION MINIMALLY INVASIVE SURGERY

CROSS REFERENCE TO RELATED APPLICATION

The present application claims the benefit of priority to Chinese Patent Application No. 2018110447946, entitled "Passage Establishment Device for Posterior Spinal Fusion Minimally Invasive Surgery", filed with CNIPA on Sep. 7, 2018, the content of which is incorporated herein by reference in its entirety.

FIELD OF THE INVENTION

The present disclosure relates to the technical field of medical equipment, in particular, to a passage establishment device for posterior spinal fusion minimally invasive surgery.

BACKGROUND

At present, problems such as difficulties in establishing an opening and maintaining the safety of a passage which is created by propping up an incision, the risk of obstructing visual fields of other surgical procedures, and the risk of causing new trauma or complications to the patient are pervasive in posterior spinal fusion minimally invasive surgery. How to design a device that can establish a passage required for a surgical approach is a problem that needs to be solved by those skilled in the art.

SUMMARY

The present disclosure provides a passage establishment device for posterior spinal fusion minimally invasive surgery, wherein a front end of the passage establishment device is configured to extend into a spine. The passage establishment device includes: a tube, wherein the tube includes a through hole penetrating both axial ends of the tube, and a wall of the tube includes an opening portion.

In some embodiments, a bottom of the tube includes a limiting protrusion portion.

In some embodiments, a plurality of elongate holes is disposed on the wall at a front part of the tube.

In some embodiments, the tube includes two tube body side portions opposite to each other; the two tube body side portions are connected by a tube body connecting portion at one side, and an interval between the two tube side portions at the other side forms the opening portion.

In some embodiments, the tube body connecting portion and each of the two tube body side portions include at least one elongate hole, respectively.

In some embodiments, a handle is disposed at a rear end of the tube.

In some embodiments, the passage establishment device for posterior spinal fusion minimally invasive surgery further includes a bottom plate, which can cover the opening portion of the tube.

In some embodiments, two protective wings spaced at an interval and extending upward are disposed at an edge of a top surface of the bottom plate, and a slot is formed at a bottom of the tube for the two protective wings to be respectively locked into.

In some embodiments, the passage establishment device for posterior spinal fusion minimally invasive surgery further includes a guide bar, wherein the structure of the guide bar is the same as the internal structure of the tube, the tube can be sleeved on the guide bar, and the guide bar is in clearance fit with the tube.

In some embodiments, the passage establishment device for posterior spinal fusion minimally invasive surgery further includes a channel positioning and expanding component. The channel positioning and expanding component includes a guide pin, an intermediate expansion kit, and an outer sleeve. The intermediate expansion kit can be sleeved on an outside of the guide pin, and the outer sleeve can be sleeved on an outside of the intermediate expansion kit. The intermediate expansion kit is in clearance fit with the guide pin. The outer sleeve is in clearance fit with the intermediate expansion kit. An outer sleeve notch is formed on an outer surface of a front part of the outer sleeve, and the outer sleeve notch communicates with an inside of the outer sleeve. An expansion portion notch is formed on an outer surface of a front end of the intermediate expansion kit. When a front end of the outer sleeve is coplanar with the front end of the intermediate expansion kit, the outer sleeve notch and the expansion portion notch form a spreading portion notch. The guide bar can be inserted into the outer sleeve, and the guide bar is in clearance fit with the outer sleeve.

One or more aspects of the passage establishment device for posterior spinal fusion minimally invasive surgery of the present disclosure has the following beneficial effects:

The tube of the passage establishment device for posterior spinal fusion minimally invasive surgery of the present disclosure can be inserted between the vertebral bodies and can also be removed from between the vertebral bodies. The through hole of the tube forms a surgical passage for the fusion device to be extended into, which can protect human tissues and makes it convenient for doctors to perform follow-up operations. The tube can be installed quickly, and thus the operation time is shortened. It is easy to disassemble, clean, and disinfect the tube.

LIST OF REFERENCE NUMERALS

100 Guide pin
200 Intermediate expansion kit
201 Expansion portion notch
210 Inner expansion tube
220 Middle expansion tube
221 Middle tube recess
222 Middle tube inclined recess
230 Outer expansion tube
231 Outer tube recess
232 Communication port
233 Outer tube inclined recess
300 Outer sleeve
310 Outer sleeve notch
320 Convex ring
400 Reamer member
410 Cutter head
420 Observation passage
430 Observation through hole
440 Handle
500 Guide bar
510 Shrinking head
520 Concave portion
600 Tube
601 Through hole
602 Tube body side portion
603 Tube body connecting portion
610 Opening portion
620 Slot
630 Limiting protrusion portion
640 Elongate hole
650 Handle
700 Bottom plate
710 Protective wing
720 Gripping plate
10 Vertebral body

DETAILED DESCRIPTION

Some embodiments of the present disclosure will be described below. Those skilled may easily understand other advantages and effects of the present disclosure according to contents disclosed by the specification.

Please refer to FIGS. 1-15. It should be understood that the structures, proportions, sizes, and the like, which are illustrated in the drawings of the present specification, are only used to clarify the contents disclosed in the specification for understanding and reading by those skilled, and are not intended to limit the implementation of the present disclosure. Any modification of the structures, change of the scales, or adjustment of the sizes should still fall within the scope of the technical contents disclosed by the present disclosure without affecting the effects and achievable objectives of the present disclosure. In the meantime, the terms "upper", "lower", "left", "right", "intermediate" and "one" as used in this specification are also for convenience of description, and are not intended to limit the scope of the present disclosure, and any change or adjustment of relative relationship without substantial changes in technology is considered to be within the scope of the present disclosure.

Referring to FIGS. 1-15, this embodiment provides a passage establishment device for posterior spinal fusion minimally invasive surgery, wherein a front end of the passage establishment device extends into a spine. The passage establishment device includes a tube 600, wherein the tube 600 includes a through hole 601 penetrating both axial ends of the tube 600, and a wall of the tube 600 includes an opening portion 610.

Figure 12:
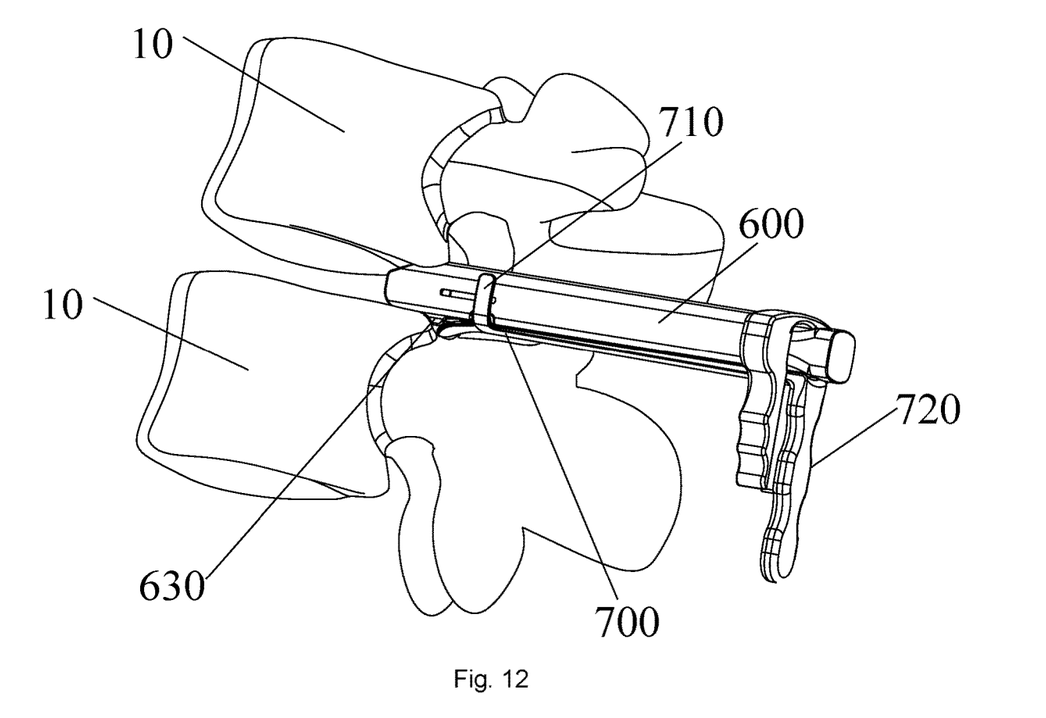
FIG. 12 shows a schematic view of a bottom plate and a tube of a passage establishment device for posterior spinal fusion minimally invasive surgery according to an embodiment of the present disclosure, wherein the bottom plate covers an opening portion of the tube and the tube is inserted between two vertebral bodies.

The tube 600 of the passage establishment device for posterior spinal fusion minimally invasive surgery of the present disclosure can be inserted between vertebral bodies 10 of a patient and can also be removed from between the vertebral bodies 10, as shown in FIG. 12. The through hole 601 of the tube 600 forms a surgical passage, into which a fusion device can be extended. The surgical passage can protect human tissues and is convenient for doctors to perform follow-up operations. In addition, the opening portion 610 of the tube 600 can be used as an outwardly extending outlet of the instrument, so that instruments of various sizes can enter the tube 600. The tube can be installed quickly, and thus the operation time is shortened. It is easy to disassemble, clean, and disinfect the tube.

Figure 14:
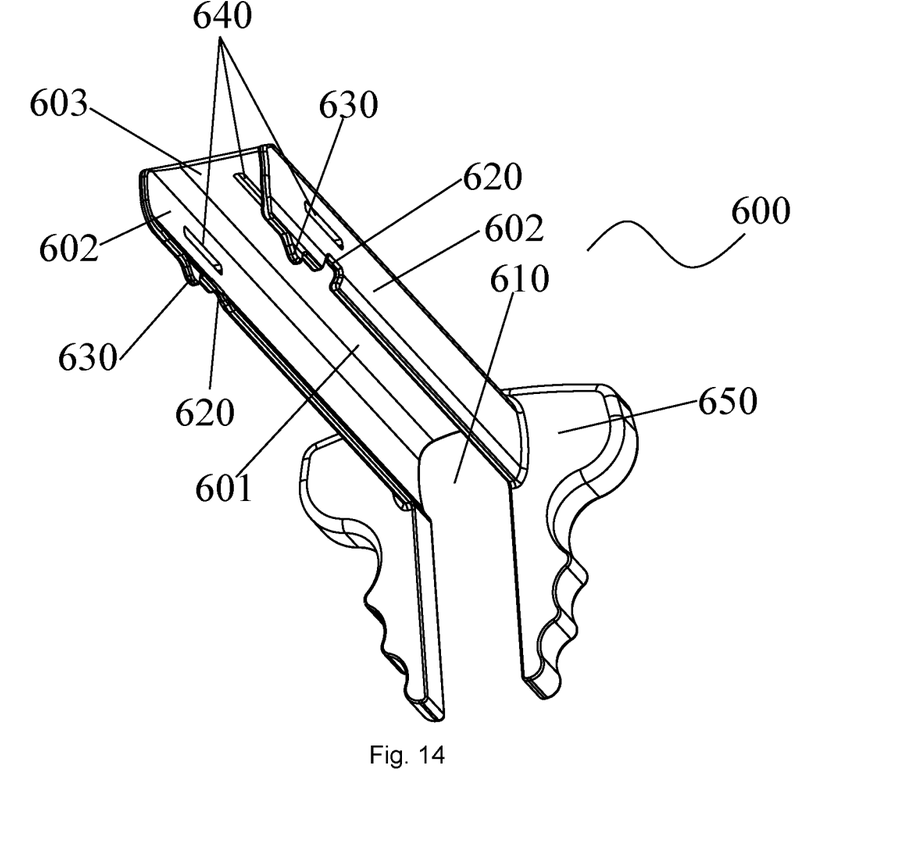
FIG. 14 shows a schematic view of a tube of the passage establishment device for posterior spinal fusion minimally invasive surgery according to an embodiment of the present disclosure.

A limiting protrusion portion 630 is disposed at a bottom of the tube 600. The limiting protrusion portion 630 limits how much of the tube 600 can enter the gap between the vertebral bodies 10, to prevent too much of the tube 600 entering the gap and affecting subsequent intervertebral treatment operations. When the front end of the tube 600 extends into the gap between the vertebral bodies 10, the limiting protrusion portion 630 contacts with the vertebral bodies 10. In this embodiment, the limiting protrusion portion 630 includes two downwardly extending noses.

A plurality of elongate holes 640 is disposed on the wall at a front part of the tube 600. The plurality of elongate holes 640 is used for visualization to observe the specific position of the tube 600 during surgery.

The tube 600 includes two tube body side portions 602 opposite to each other, the two tube body side portions 602 are connected by a tube body connecting portion 603 at one side, and an interval between the two tube side portions 602 at the other side forms the opening portion 610. This arrangement makes the structure of the tube 600 more stable. In this embodiment, the two oppositely disposed tube body side portions 602 are parallel, and each of the tube body side portions 602 is perpendicular to the tube body connecting portion 603. This structure facilitates the processing of the tube 600. The two noses are arranged on the two tube body side portions 602 respectively.

The tube body connecting portion 603 and each of the two tube body side portions 602 include at least one elongate hole 640, respectively, so that the tube 600 can be used to visualize the operation location at various angles.

A handle 650 is disposed at the rear end of the tube 600 to facilitate the medical staff to hold the tube 600.

Figure 15:
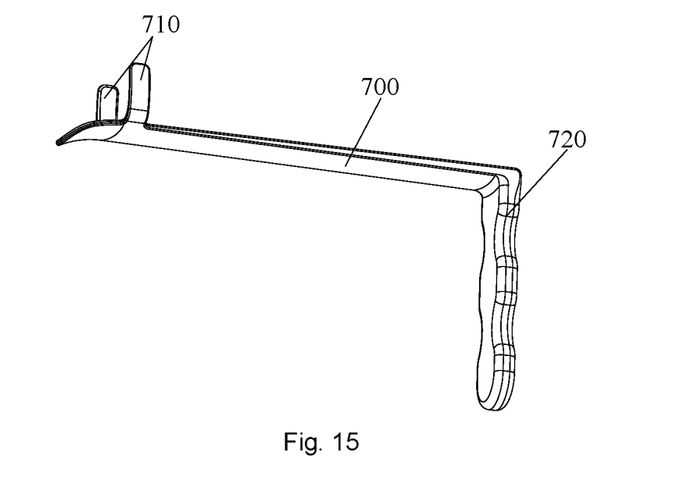
FIG. 15 shows a schematic view of a bottom plate of the passage establishment device for posterior spinal fusion minimally invasive surgery according to an embodiment of the present disclosure.

The passage establishment device for posterior spinal fusion minimally invasive surgery further includes a bottom plate 700, which can cover the opening portion 610 of the tube 600. The bottom plate 700 covers the opening portion 610 of the tube 600, and the bottom plate 700 and the tube 600 enclose a surgical passage into which the fusion device is extended. Since the bottom plate 700 and the tube 600 are not fixedly connected, the bottom plate 700 blocks muscles from entering the through hole 601 of the tube 600, and when a device extended in the tube 600 is stretched outwards, it can also abut on the bottom plate 700.

Two protective wings 710 spaced at an interval and extending upward are disposed at an edge of a top surface of the bottom plate 700, and two slots 620 are disposed at a bottom of the tube 600, into which the two protective wings 710 are respectively locked. The two slots 620 are matched with the two protective wings 710 of the bottom plate 700, so that when the protective wings 710 of the bottom plate 700 are pushed to the slots 620, the protective wings 710 can be locked into the slots 620. After the two protective wings 710 are respectively locked into the slots 620, the two protective wings 710 clamp the tube 600. This structure can restrict the bottom plate 700 from moving sideways after being inserted into the human body. In this embodiment, the two protective wings 710 are located at the front part of the bottom plate 700. In this embodiment, the two slots 620 are disposed on the two tube body side portions 602 respectively.

In operation, the front end of the bottom plate 700 is tilted downward to prevent the bottom plate 700 from entering the intervertebral disc and affecting subsequent intervertebral treatment operations. A gripping plate 720 extending downward is disposed at the rear end of the bottom plate 700, and the gripping plate 720 makes it convenient for medical personnel to hold the bottom plate 700.

Figure 11:
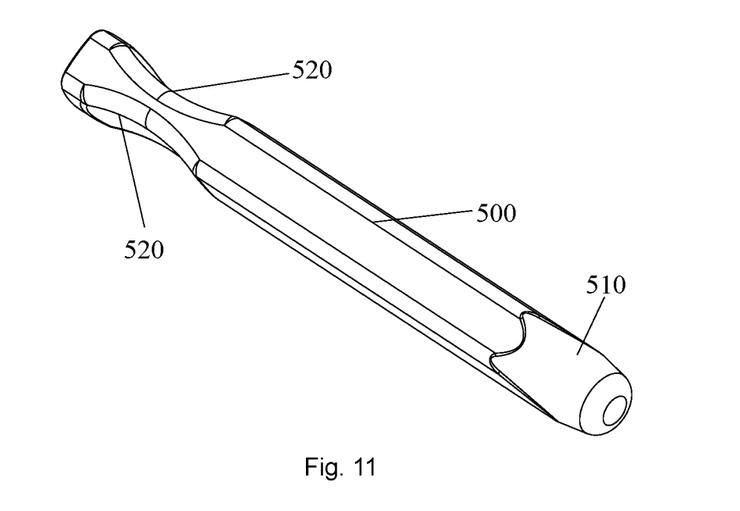
FIG. 11 shows a schematic view of a guide bar of a passage establishment device for posterior spinal fusion minimally invasive surgery according to an embodiment of the present disclosure.
Figure 13:
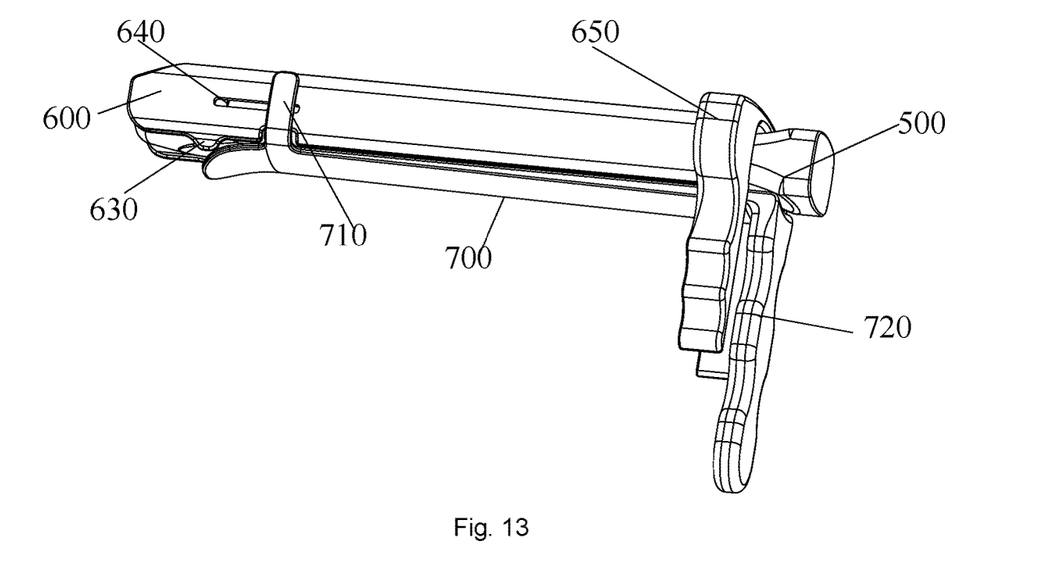
FIG. 13 shows a schematic view of a bottom plate, a tube, and a guide bar of a passage establishment device for posterior spinal fusion minimally invasive surgery according to an embodiment of the present disclosure, wherein the bottom plate covers an opening portion of the tube and the guide bar is inserted between the bottom plate and the tube.

The passage establishment device for posterior spinal fusion minimally invasive surgery further includes a guide bar 500. The structure of the guide bar 500 is substantially the same as the internal structure of the tube 600. The tube 600 can be sleeved on the guide bar 500, and the guide bar 500 is in clearance fit with the tube 600. Before the tube 600 extends between the vertebral bodies 10, the guide bar 500 extends between the vertebral bodies 10 to play a guiding role.

Figure 10:
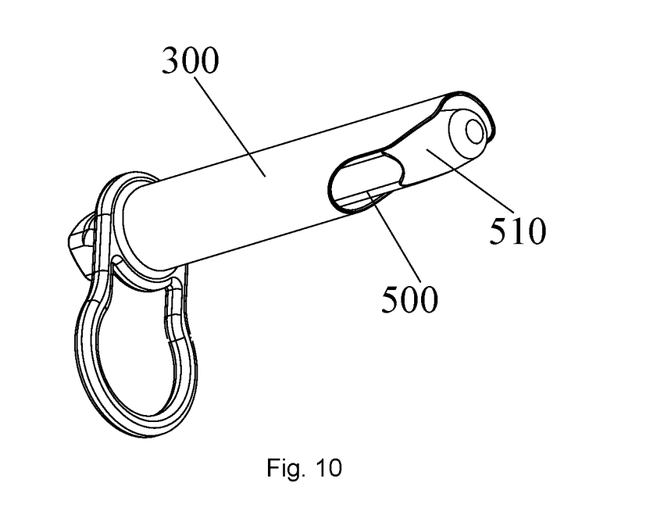
FIG. 10 shows a schematic view of a guide bar and an outer sleeve of a passage establishment device for posterior spinal fusion minimally invasive surgery according to an embodiment of the present disclosure, wherein the guide bar is inserted into the outer sleeve.

In this embodiment, a cross section of the guide bar 500 is rectangular, and the length of the cross section of the guide bar 500 is greater than the width of the cross section of the guide bar 500. The guide bar 500 is in clearance fit with the outer sleeve 300. When the guide bar 500 is inserted into the outer sleeve 300, the longitudinal direction of the cross section of the guide bar 500 is substantially horizontal.

A shrinking head 510 is disposed at the front part of the guide bar 500, and the shrinking head 510 is a structure that tapers in the forward direction. Concave portions 520 are formed on both a top surface and a bottom surface of the rear portion of the guide bar 500.

The shrinking head 510 is a structure that tapers in the forward direction, which facilitates guidance, so that the guide bar 500 can be easily inserted into the gap between the vertebral bodies 10. The concave portions 520 are formed on both the top surface and the bottom surface of the rear portion of the guide bar 500, so that the guide bar 500 forms two concave portions 520 in the flat direction. The two concave portions 520 may indicate to the doctor the direction in which the guide bar 500 enters the gap between the vertebral bodies 10, and also facilitate grasping.

Figure 1:
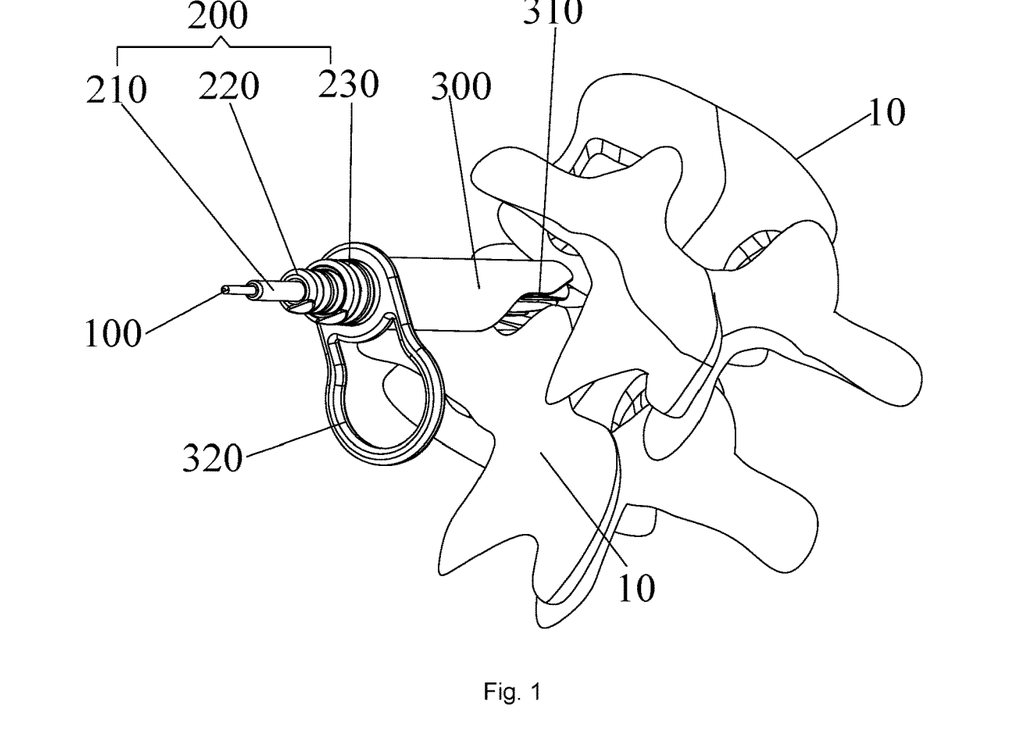
FIG. 1 shows a schematic view of a guide pin, an inner expansion tube, a middle expansion tube, an outer expansion tube, and an outer sleeve of a passage establishment device for posterior spinal fusion minimally invasive surgery according to an embodiment of the present disclosure, wherein the guide pin is inserted between two vertebral bodies, and the tubes, and the outer sleeve are sequentially sleeved on the guide pin.
Figure 2:
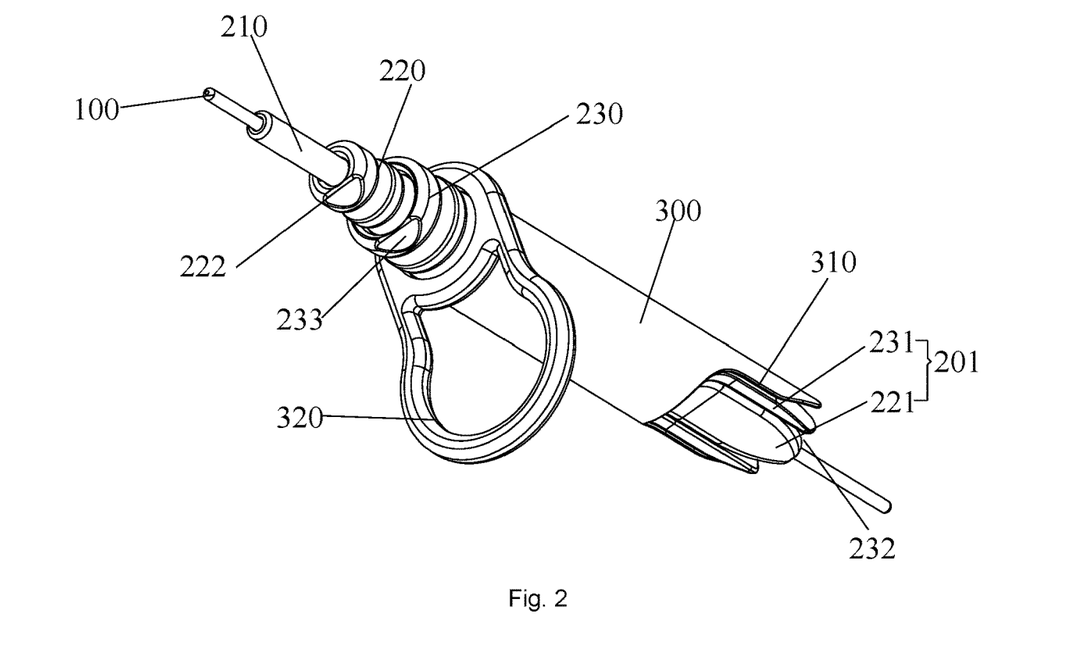
FIG. 2 shows a schematic view of a guide pin, an inner expansion tube, a middle expansion tube, an outer expansion tube, and an outer sleeve of a passage establishment device for posterior spinal fusion minimally invasive surgery according to an embodiment of a present disclosure, wherein the tubes, and the outer sleeve are sequentially sleeved on the guide pin.
Figure 3:
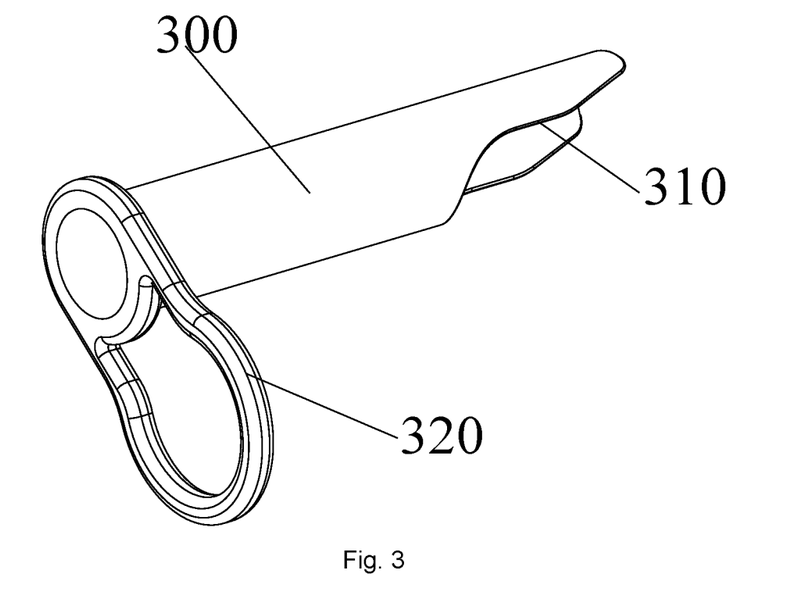
FIG. 3 shows a schematic view of an outer sleeve of a passage establishment device for posterior spinal fusion minimally invasive surgery according to an embodiment of the present disclosure.

The passage establishment device for posterior spinal fusion minimally invasive surgery further includes a channel positioning and expanding component. The channel positioning and expanding component includes a guide pin 100, an intermediate expansion kit 200, and an outer sleeve 300. The intermediate expansion kit 200 can be sleeved on the outside of the guide pin 100, and the outer sleeve can be sleeved on the outside of the intermediate expansion kit 200. The intermediate expansion kit 200 is in clearance fit with the guide pin 100. The outer sleeve 300 is in clearance fit with the intermediate expansion kit 200. An outer sleeve notch 310 is disposed on an outer surface of a front part of the outer sleeve 300, and the outer sleeve notch 310 communicates with the inside of the outer sleeve 300. An expansion portion notch 201 is formed on an outer surface of a front end of the intermediate expansion kit 200. When a front end of the outer sleeve 300 is coplanar with the front end of the intermediate expansion kit 200, the outer sleeve notch 310 and the expansion portion notch 201 form a spreading portion notch. The guide bar 500 can be inserted into the outer sleeve 300, and the guide bar 500 is in clearance fit with the outer sleeve 300.

When the passage establishment device for posterior spinal fusion minimally invasive surgery of the present disclosure is being used, the guide pin 100 is first inserted into the predetermined approach for positioning, and then the intermediate expansion kit 200 and the outer sleeve 300 are sequentially sleeved on the guide pin 100 to increase the size of the required surgical passage. After the outer sleeve 300 reaches the intervertebral disc, the intermediate expansion kit 200 and the guide pin 100 are pulled out. The guide bar 500 is then inserted into the outer sleeve 300, and the guide bar 500 extends into the gap between the vertebral bodies 10. After the outer sleeve 300 is pulled out, the tube 600 is sleeved on the guide bar 500. After the guide bar 500 is pulled out, the bottom plate 700 is inserted under the tube 600. Since the bottom plate 700 covers the opening portion 610 of the tube 600, the bottom plate 700 and the tube 600 enclose a surgical passage into which the fusion device is extended. Each part of the passage establishment device of the present disclosure is an independent structure, so that the device can be easily disassembled and cleaned and disinfected.

Figure 7:
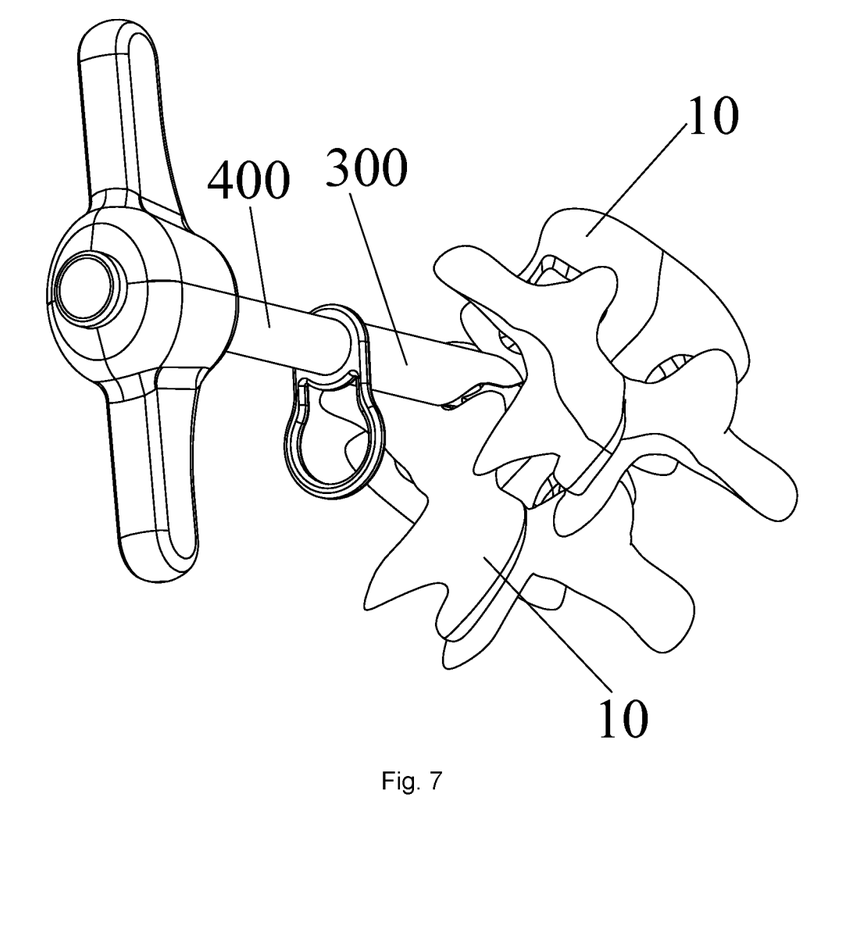
FIG. 7 shows a schematic view of a reamer member and an outer sleeve of a passage establishment device for posterior spinal fusion minimally invasive surgery according to an embodiment of the present disclosure, wherein the reamer member is inserted in the outer sleeve.
Figure 8:
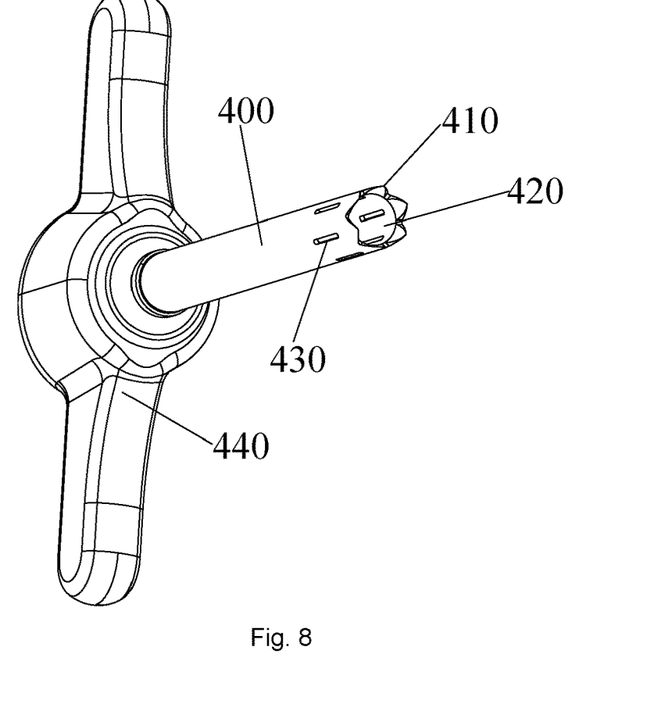
FIG. 8 shows a schematic view of a reamer member of a passage establishment device for posterior spinal fusion minimally invasive surgery according to an embodiment of the present disclosure.
Figure 9:
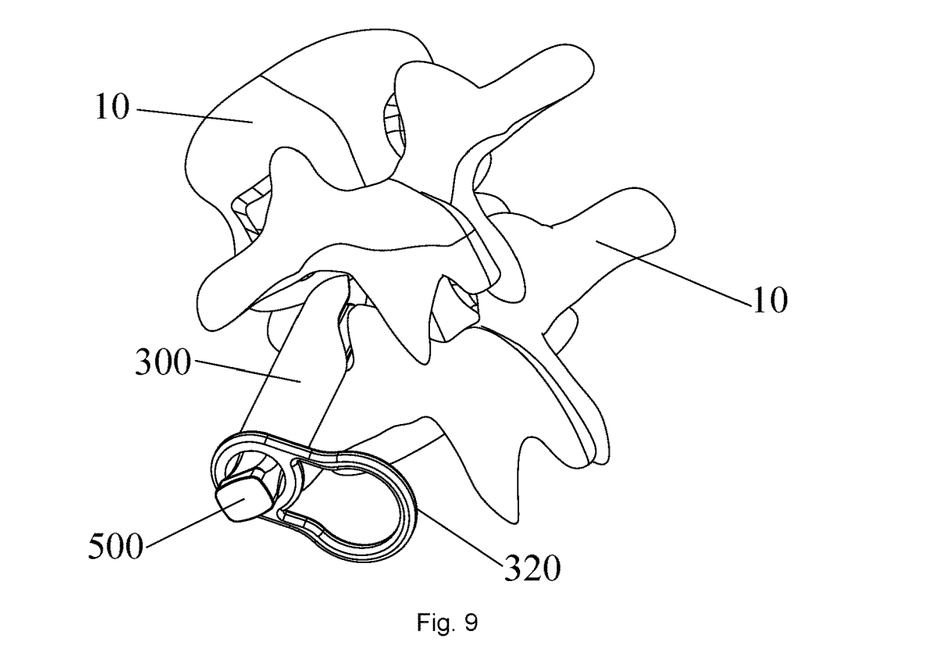
FIG. 9 shows a schematic view of a guide bar and an outer sleeve of a passage establishment device for posterior spinal fusion minimally invasive surgery according to an embodiment of the present disclosure, wherein the guide bar is inserted into the outer sleeve and between two vertebral bodies.

The passage establishment device for posterior spinal fusion minimally invasive surgery further includes a reamer member 400. The reamer member 400 may be inserted into the outer sleeve 300, and a cutter head 410 is disposed at the front end of the reamer member 400. In operation, the intermediate expansion kit 200 and the guide pin 100 are pulled out before the reamer member 400 is inserted into the outer sleeve 300, and then the cutter head 410 of the reamer member 400 cuts off the part of the spinous process that blocks the surgical passage. After the reamer member 400 is pulled out, the guide bar 500 is inserted into the outer sleeve 300.

The spreading portion notch effectively enables the passage establishment device to avoid tissues, such as the spinous process, below the passage establishment device during the approaching. The setting of the outer sleeve notch 310 helps to avoid the tissue during insertion, and at the same time free up the working area of the reamer member 400, so that the reamer member 400 can remove the spinous process blocking the approach.

In this embodiment, the diameter of the guide pin 100 is 1.5 mm. The outer sleeve notch 310 extends from one third of the outer sleeve 300 along the length direction of the outer sleeve 300, and extends to the front end of the outer sleeve notch 300

The inner and outer sides of the intermediate expansion kit 200 are both cylindrical, the outer side of the guide pin 100 is cylindrical, and the inner diameter of the intermediate expansion kit 200 is equal to the outer diameter of the guide pin 100. The inner side of the outer sleeve 300 is cylindrical, and the inner diameter of the outer sleeve 300 is equal to the outer diameter of the intermediate expansion kit 200. The length of the cross section of the guide bar 500 is equal to the inner diameter of the outer sleeve 300. This structure is convenient for processing and installation.

The intermediate expansion kit 200 includes at least two expansion tubes sleeved together in the radial direction. A second expansion tube of the at least two expansion tubes is in clearance fit with, and sleeved on, a first expansion tube of the at least two expansion tubes; when there is a third expansion tube, the third expansion tube is in clearance fit with, and sleeved on, the second expansion tube, and so on.

The innermost expansion tube of the at least two expansion tubes, i.e. the first expansion tube, may be sleeved outside the guide pin 100. The inner diameter of the innermost expansion tube is equal to the outer diameter of the guide pin 100, and the innermost expansion tube has a clearance fit with the guide pin 100. The outermost expansion tube may be sleeved with an outer sleeve 300. The outer diameter of the outermost expansion tube is equal to the inner diameter of the outer sleeve 300, and the outermost expansion tube has a clearance fit with the outer sleeve 300.

The intermediate expansion kit 200 includes at least two expansion tubes that are sleeved together in the radial direction, so that the size of the required surgical passage can be gradually increased, thereby avoiding trauma to human tissues caused by violently expanding the surgical passage. Since each two adjacent expansion tubes are in clearance fit, the surgical passage required for progressive expansion can be realized.

Figure 4:
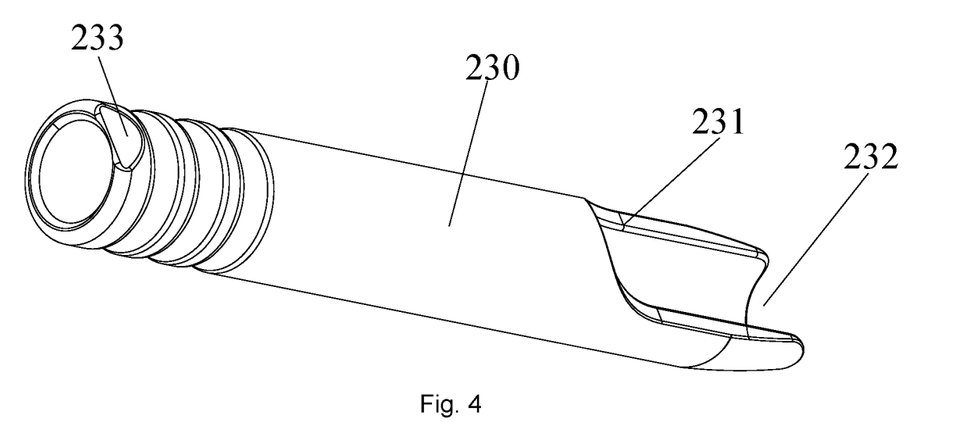
FIG. 4 shows a schematic view of an outer expansion tube of a passage establishment device for posterior spinal fusion minimally invasive surgery according to an embodiment of the present disclosure.
Figure 5:
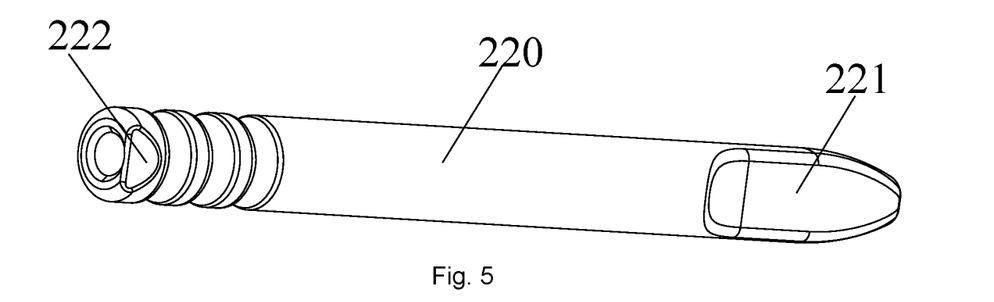
FIG. 5 shows a schematic view of a middle expansion tube of a passage establishment device for posterior spinal fusion minimally invasive surgery according to an embodiment of the present disclosure.
Figure 6:
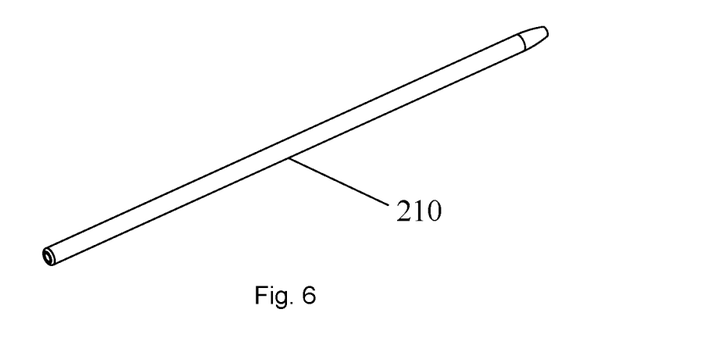
FIG. 6 shows a schematic view of an inner expansion tube of a passage establishment device for posterior spinal fusion minimally invasive surgery according to an embodiment of the present disclosure.

The intermediate expansion kit 200 includes three expansion tubes in some embodiments, and the three expansion tubes are respectively, from the innermost one to the outermost one, an inner expansion tube 210, a middle expansion tube 220, and an outer expansion tube 230. A part of the wall of the middle expansion tube 220 is recessed from the outside to the inside of the middle expansion tube 220 to form a middle tube recess 221, and the middle tube recess 221 extends to the front end of the middle expansion tube 220. A part of the wall of the outer expansion tube 230 is recessed from the outside to the inside of the outer expansion tube 230 to form an outer tube recess 231. The outer tube recess 231 extends to the front end of the outer expansion tube 230, and a communication port 232 is disposed at the bottom of the outer tube recess 231 to communicate with the inside of the outer expansion tube 230. When the front end of the middle expansion tube 220 and the front end of the outer expansion tube 230 are coplanar, the middle tube recess 221 and the outer tube recess 231 form the expansion portion notch 201.

In this embodiment, the intermediate expansion kit 200 includes three expansion tubes, and this structure facilitates the realization of progressive expansion passages. The middle tube recess 221 and the outer tube recess 231 form the expansion portion notch 201, which provides the expansion portion notch 201 with a relatively high recess depth, and effectively enables the passage establishment device to avoid tissues such as spinous processes below the approach.

The middle tube recess 221 extends from one third of the middle expansion tube 220 along the axial direction of the middle expansion tube 220. The outer tube recess 231 extends from one third of the outer expansion tube 230 along the length direction of the outer expansion tube 230.

A middle tube inclined recess 222 is disposed at the rear end of the middle expansion tube 220, and the middle tube inclined recess 222 and the middle tube recess 221 are on the same side of the middle expansion tube 220. An outer tube inclined recess 233 is disposed at the rear end of the outer expansion tube 230, and the outer tube inclined recess 233 and the outer tube recess 231 are on the same side of the outer expansion tube 230. This structure enables the medical staff to know the direction and position of the middle tube recess 221 and the outer tube recess 231 during insertion, so that the middle expansion tube 220 and the outer expansion tube 230 can be inserted into the human body at a correct angle.

The reamer member 400 is in clearance fit with the outer sleeve 300. The outer diameter of the reamer member 400 is equal to the inner diameter of the outer sleeve 300, so that the cutter head 410 of the reamer member 400, inserted into the outer sleeve 300, may directly extend from the outer sleeve notch 310, and the cutter head 410 may cut part of the spinous process. The outer side of the reamer member 400 is cylindrical, and the outer diameter of the reamer member 400 is equal to the inner diameter of the outer sleeve 300. This structure facilitates the installation and processing of the reamer member 400.

The reamer member 400 includes an observation passage 420, which extends from the front ends of the reamer member 400 to the rear ends of the reamer member 400. A plurality of observation through holes 430 is disposed on the inner side wall at the front part of the observation passage 420, and all the observation through holes 430 are evenly distributed along the circumference of the observation passage 420. A cross-section of the observation passage 420 is circular, with the cutting plane substantially perpendicular to the axis of the observation passage 420, and the diameter of a central through hole of the observation passage 420 is 10 mm. The observation passage 420 can facilitate the medical personnel to insert an observation device such as an endoscope during the cutting process, which further facilitates inspection of the vicinity of the reamer member 400.

In this embodiment, the diameter of the observation passage 420 is 10 mm. The number of the observation through holes 430 is six. The observation through holes 430 are oblong holes. And the observation through holes 430, along with imaging equipment, are used for visualization during surgery, which aids the medical staff in knowing the specific location of the scalpel in the human body. All the observation through holes 430 are located behind the cutter head 410. A handle 440 is installed on the rear end of the reamer member 400.

A convex ring 320 is disposed at the rear end of the outer sleeve 300, and the convex ring 320 and the outer sleeve notch 310 are located on the same side of the outer sleeve 300. This structure allows the medical staff to know the orientation of the outer sleeve notch 310.

A method of using the passage establishment device for posterior spinal fusion minimally invasive surgery of the present disclosure includes the following operations:

1) anchoring the device by inserting the guide pin 100 on a predetermined approach;
2) sequentially placing the inner expansion tube 210, the middle expansion tube 220, the outer expansion tube 230, and the outer sleeve 300 on the guide pin 100 to increase the size of the required surgical passage;
3) after the outer sleeve 300 reaches the intervertebral disc, pulling out the inner tube 210, the middle tube 220, the outer expansion tube 230, and the guide pin 100;
4) inserting the reamer member 400 into the outer sleeve 300, after which the cutter head 410 of the reamer member 400 cuts off part of the spinous process that blocks the surgical passage;
5) after pulling out the cutter head 410 of the reamer member 400, inserting the guide bar 500 into the outer sleeve 300, with the guide bar 500 extending into the gap between the vertebral bodies 10;
6) after pulling out the outer sleeve 300, sleeving the tube 600 on the guide bar 500, with the tube 600 extending into the gap of the vertebral bodies 10;
7) after pulling out the guide bar 500, inserting the bottom plate 700 under the tube 600, with the bottom plate 700 and the tube 600 enclosing a surgical passage for the fusion device to be extended into, since the bottom plate 700 covers the opening portion 610 of the tube 600; and
8) operating between the vertebral bodies 10 through the surgical passage, and then inserting the fusion device; and after inserting the fusion device, pulling out the tube 600 and the bottom plate 700 before performing subsequent incision sutures.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:
1. A passage establishment device for posterior spinal fusion minimally invasive surgery, wherein a front end of the passage establishment device extends into a spine, wherein the device comprises:
   a tube (600), wherein an interior of the tube (600) includes a through hole (601) penetrating both axial ends of the tube (600), and a wall of the tube (600) includes an opening portion (610);
   wherein a plurality of elongate holes (640) is formed on the wall at a front part of the tube (600);
   wherein the tube (600) comprises two tube body side portions (602) opposite to each other,
   wherein the two tube body side portions (602) are connected by a tube body connecting portion (603) at one side,
   wherein an interval between the two tube side portions (602) at the other side forms the opening portion (610); and
   wherein the tube body connecting portion (603) and each of the two tube body side portions (602) include at least one of the plurality of elongate holes (640), respectively.

2. The passage establishment device for posterior spinal fusion minimally invasive surgery according to claim 1, wherein a bottom of the tube (600) includes a limiting protrusion portion (630).

3. The passage establishment device for posterior spinal fusion minimally invasive surgery according to claim 1, wherein a handle (650) is disposed at a rear end of the tube (600).

4. The passage establishment device for posterior spinal fusion minimally invasive surgery according to claim 1, further comprising a bottom plate (700), which covers the opening portion (610) of the tube (600).

5. The passage establishment device for posterior spinal fusion minimally invasive surgery according to claim 4, wherein two protective wings (710) spaced at an interval and extending upward are disposed at an edge of a top surface of the bottom plate (700), and slots (620) are disposed at a bottom of the tube (600) for the two protective wings (710) to be respectively locked into.

6. The passage establishment device for posterior spinal fusion minimally invasive surgery according to claim 1, wherein the tube (600) can be sleeved on a guide bar (500), wherein the structure of the guide bar (500) is the same as the internal structure of the tube (600), and the guide bar (500) is in clearance fit with the tube (600).

7. A passage establishment system for posterior spinal fusion minimally invasive surgery, comprising:
   a guide pin (100);
   an intermediate expansion kit (200), wherein the intermediate expansion kit (200) can be sleeved on an outside of the guide pin (100), wherein the intermediate expansion kit (200) is in clearance fit with the guide pin (100),
   wherein an expansion portion notch (201) is formed on an outer surface of a front end of the intermediate expansion kit (200);
   an outer sleeve (300), wherein the outer sleeve (300) can be sleeved on an outside of the intermediate expansion kit (200), wherein the outer sleeve (300) is in clearance fit with the intermediate expansion kit (200),
   wherein an outer sleeve notch (310) is formed on an outer surface of a front part of the outer sleeve (300), wherein the outer sleeve notch (310) communicates with the inside of the outer sleeve (300),
   wherein when a front end of the outer sleeve (300) is coplanar with the front end of the intermediate expansion kit (200), the outer sleeve notch (310) and the expansion portion notch (201) form a spreading portion notch;

a guide bar (500), wherein the guide bar (500) can be inserted into the outer sleeve (300), wherein the guide bar (500) is in clearance fit with the outer sleeve (300); and a passage establishment device for posterior spinal fusion minimally invasive surgery, wherein a front end of the passage establishment device extends into a spine, wherein the device comprises:

a tube (600), wherein an interior of the tube (600) includes a through hole (601) penetrating both axial ends of the tube (600), and a wall of the tube (600) includes an opening portion (610), wherein the internal structure of the tube (600) is the same as the structure of the guide bar (500), the tube (600) can be sleeved on the guide bar (500), and the guide bar (500) is in clearance fit with the tube (600).

* * * * *